(12) United States Patent
Mendoza

(10) Patent No.: US 6,227,936 B1
(45) Date of Patent: May 8, 2001

(54) HANDS FREE PUMPING AND NURSING BRA

(76) Inventor: Amelia Mendoza, 18041 Acre St., Northridge, CA (US) 91325

(*) Notice: Subject to any disclaimer, the term of this patent is extended or adjusted under 35 U.S.C. 154(b) by 0 days.

(21) Appl. No.: 09/399,374

(22) Filed: Sep. 20, 1999

(51) Int. Cl.⁷ ........................................... A41C 3/04
(52) U.S. Cl. .................... 450/36; 450/58; 450/8; 450/9; 2/104
(58) Field of Search ................. 450/36, 33, 58, 450/72, 82, 31, 32, 54, 7–10, 14, 15, 17, 18; 2/104, 101, 271

(56) References Cited

U.S. PATENT DOCUMENTS

| 949,414 | 2/1910 | Cunningham . | |
|---|---|---|---|
| 2,436,430 | 2/1948 | Hart . | |
| 2,492,862 | 12/1949 | Harvey . | |
| 2,585,338 | 2/1952 | Meares . | |
| 2,613,355 | 10/1952 | Coleman . | |
| 3,002,515 | * 10/1961 | Glogover | ................................ 450/36 |
| 4,335,728 | 6/1982 | Fildan . | |
| 4,640,287 | 2/1987 | Anderson et al. . | |
| 4,878,879 | 11/1989 | Kunstadter . | |
| 5,380,238 | 1/1995 | Crew-Gee . | |
| 5,514,166 | 5/1996 | Silver et al. . | |
| 5,575,768 | 11/1996 | Lockridge et al. . | |
| 5,616,125 | 4/1997 | Jelks . | |
| 6,027,396 | * 2/2000 | Yonchar | ................................ 450/36 |

FOREIGN PATENT DOCUMENTS

| 919893 | 3/1947 | (FR) . |
|---|---|---|
| 881406 | 7/1950 | (FR) . |

* cited by examiner

*Primary Examiner*—Gloria M. Hale
(74) *Attorney, Agent, or Firm*—Hoffman, Wasson & Gitler

(57) ABSTRACT

A hands free pumping and nursing brassiere that operates similar to a regular nursing bra, yet differs in that it has a detachable hands free pumping panel positioned behind the nursing cup. To nurse, a woman detaches the nursing cup with the pumping panel attached thereto. To perform hand free pumping, the nursing cup is detached from the pumping panel, a breast shield is inserted from the back of the pumping panel through an opening in the pumping panel, so that it can be attached to the pump. The pumping panel is then reattached to the brassiere allowing the woman to pump her breast milk in a hands free manner.

22 Claims, 8 Drawing Sheets

HANDS FREE PUMPING AND NURSING BRA

BACKGROUND OF THE INVENTION

1. Field of the Invention

The present invention relates to a hands free pumping and nursing brassiere. More particularly, the present invention relates to a brassiere which can be used in one mode, in a conventional manner, to nurse a child and can be used in a second mode to support breast pumps while leaving the mother's hands free.

2. Description of the Prior Art

In response to recent studies detailing the benefits of breast milk for newborn children and the American Academy of Pediatrics recommendation that women breast feed for a minimum of one year, the number of women, and the length of time women breast feed is increasing.

The most common way for an infant to receive breast milk is by directly nursing on a woman's breast. To facilitate such breast feeding, numerous nursing brassieres are well known. These nursing brassieres allow the woman wearing them to expose sufficient breast tissue to allow the child to latch on to her breast and nurse.

While direct nursing has been used for hundreds of years, there are drawbacks to this technique. For example, it is not possible to monitor how much breast milk a child is receiving during breast feeding. Also, some children do not latch on correctly, and as a result do not receive enough nutrition. From the nursing mother's point of view there are other drawbacks, such as, sore nipples and sleep deprivation due to frequent feedings. In addition, mothers who return to work need to express their milk every 2 to 3 hours in order to maintain their milk supply and to provide a supply of milk for their baby while they are away. To overcome these problems, various breast pumps have been developed to express milk from the mother's breasts. These pumps are either manual pumps with a piston-like mechanism, or electric pumps. Both types of pumps usually have a conical pump shield that fits around the woman's nipple and facilitates the creation of a vacuum to express milk from the breast and collect it.

The use of such breast pumps can be difficult and awkward. The manual pumps are especially difficult as the mother has to hold the pump in place with one hand and operate the pump with the other hand. This leaves no hands free to see to the newborn's needs or to attend to other tasks, during pumping. The electric pumps, while not requiring a hand to operate, require the mother to hold the pump shield in place with at least one hand.

While a nursing mother can wear a nursing brassiere for proper support, and such a brassiere does not impede expressing milk with a pump, there is a need for some device that can support the mother's breasts, allow for direct nursing, and which holds a breast pump in place during expressing of milk, thereby leaving the mother's hands free. Such a device has to take into account the fact that the weight of the pump increases as milk is expressed, and therefore the device must be strong enough to maintain the pump in position even when full (at least 5 ounces and as much as 8 ounces).

One attempt at such a device is shown in U.S. Pat. No. 5,514,166 (Silver et al.) which discloses a device and method for supporting a breast shield and related pump equipment. In the embodiment of FIG. 1, a brassiere 12 having two breast cups 20 is provided. Each of the breast cups 20 has a flap 28 connected to the brassiere at the bottom of each cup 20. The cup is detachably connected to the brassiere near the shoulder strap 29. In FIGS. 3, 4, 5, 6, 11 and 12 of the Silver et al. patent, a breast pump 30 (shown in FIG. 2), having a breast shield or hood 32, can be amended with various fastener arrangements so that it can be attached to the cup 20.

In the embodiments of FIGS. 7, 9, 10, 18 and 19 of the Silver et al. patent, the breast shield 32 of the breast pump 30 is inserted through the flap 28 of the brassiere 12 so that the breast shield 32 is supported on the breast 14 between the breast 14 and the inside surface of the flap 28. These embodiments rely upon the flap 28 and a stiffened peripheral edge 590 of the breast shield 32 to cooperate to support the breast shield on the breast. In addition, the embodiment shown in FIG. 9 of the Silver patent employs an additional strap.

In the embodiment shown in FIG. 8 of the Silver et al. patent, a flap 628 is provided and has two overlapping sections 691 and 692. The breast shield is inserted through the front of the brassiere cup and relies on sections 691 and 692 to surround the breast shield and support it against the breast. Such an arrangement would prevent a mother from nursing.

In the embodiment shown in FIG. 10 of the Silver et al patent, the breast cup 20 may have a crisscrossed overlap portion 803. The crisscrossed overlap portion has an opening sufficient to allow insertion of the breast shield and is relied upon to surround the breast shield and to support it against the breast.

In the embodiment shown in FIGS. 13 and 14 of the Silver et al. patent, a strap 1022 is relied upon to support the breast shield 32 of the breast pump 30. The breast shield 32 is placed near the breast and the strap 1022 is fastened around the pump shield. The breast shield 32 is placed on the breast 14 and supported by the strap 1022.

The device taught in Silver et al. suffers from numerous disadvantages. First, the embodiments requiring fasteners, are cumbersome and bulky. In addition, pump shield designs vary between manufacturers and therefore not every fastener would work for each breast pump.

Second, the embodiments that do not employ fasteners will not provide sufficient force upon the breast shield to maintain the shield against the breast in such a way that sufficient vacuum can be maintained. All of the embodiments of the Silver et al. device require the breast shield to be inserted from the front of the brassiere. As a result, in order for the breast shield to fit through an opening in the cup, which is smaller than the diameter of the breast shield, the material of the cup must be elastic or flexible. Such material will not provide sufficient pressure against the breast shield as it fills with milk.

Furthermore, in the embodiments utilizing straps to secure the breast shield against the breast, the straps are not arranged so that they create even pressure all the way around the breast shield, and thus reduce the capability of the device to keep the breast shield properly positioned against the breast to maintain the necessary vacuum.

Finally, the device according to Silver et al. does not provide a simple design that is easy to utilize, provides clean lines when used solely as a breast support, and provides adequate pressure to create and maintain a vacuum between the breast shield and the breast during pumping.

From the foregoing, it is an object of the present invention to provide a hands free pumping and nursing brassiere that creates appealing contours in the brassiere when not used for pumping or nursing.

Another object of the present invention is to provide a hands free pumping and nursing brassiere that can support the mother's breasts, allow for direct nursing, and which holds a breast pump in place during expressing of milk, thereby leaving the mother's hands free.

Yet another object of the present invention is to provide a hands free pumping and nursing brassiere that does not employ fasteners to support the breast shield of a pump, and yet will provide sufficient force upon the breast shield to maintain the shield against the breast in such a way that sufficient vacuum can be maintained.

Still another object of the present invention is to provide a hands free pumping and nursing brassiere that creates even pressure all the way around the breast shield and thus keeps the breast shield of a breast pump properly positioned against the breast to maintain the necessary vacuum.

Another object of the present invention is to provide a hands free pumping and nursing brassiere that is easy to utilize, provides clean lines when used solely as a breast support, and provides adequate pressure to create and maintain a vacuum between the breast shield and the breast during pumping.

Yet another object of the present invention is to provide a hands free pumping and nursing brassiere that can be used with a number of different manufacturer's breast pumps.

SUMMARY OF THE INVENTION

These and other deficiencies of the prior art are addressed by the present invention which is directed to a hands free pumping and nursing brassiere that operates similar to a regular nursing brassiere, yet differs in that it has a detachable hands free pumping panel positioned behind the nursing cup. To nurse, a woman detaches the nursing cup with the pumping panel attached thereto. To perform hand free pumping, the nursing cup is detached from the pumping panel, a breast shield is inserted from the back of the pumping panel through an opening in the pumping panel, so that it can be attached to the pump. The pumping panel is then reattached to the brassiere allowing the woman to pump her breast milk in a hands free manner.

BRIEF DESCRIPTION OF THE DRAWINGS

These and other attributes of the present invention will be described with respect to the following drawings in which.

DETAILED DESCRIPTION OF THE INVENTION

Figure 1:
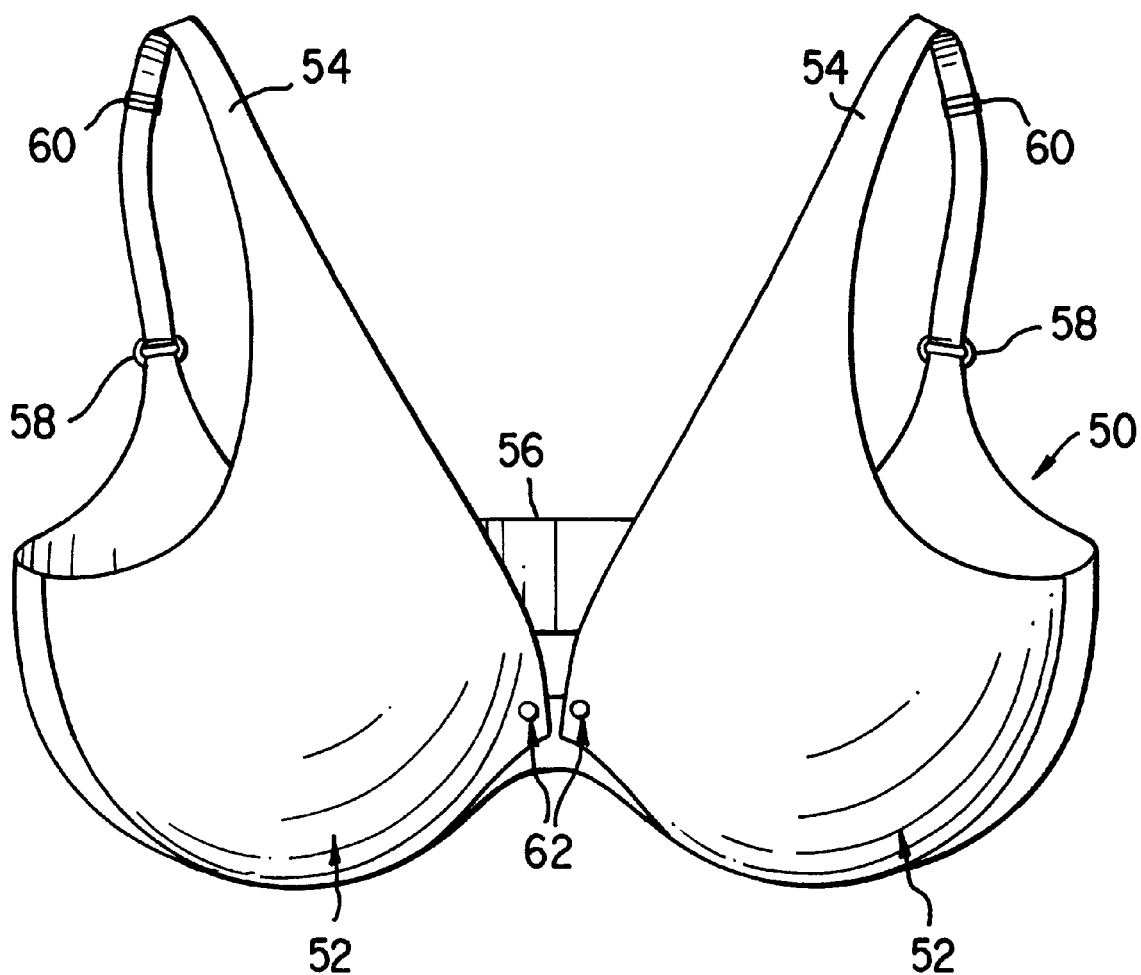
FIG. 1 is a front perspective view of the outside of the hands free pumping and nursing brassiere according to the present invention.

Referring to FIG. 1, a perspective view of the outside of the hands free pumping and nursing brassiere 50 according to the present invention is shown. The brassiere 50 has two nursing cups 52, two shoulder straps 54, and a back and side strap 56 that wraps around the torso and connects at the middle of a woman's back. The shoulder straps 54 are connected to the back and side strap 56 by metal or plastic circles or rings 58. The shoulder straps 54 may further have strap adjusters 60. The strap adjusters 60 may be of any conventional type.

The nursing cups 52 each have snaps or fasteners 62 provided at the juncture of the two nursing cups 52, which lies over the women's breast bone when worn. While snaps are shown in the illustrated embodiment, other types of fasteners such as buttons or hook-and-loop type fasteners may be employed. Furthermore, the snaps or fasteners 62 may be made of metal or plastic. The nursing cups 52 may be made from any type of suitable cloth.

Figure 2A:
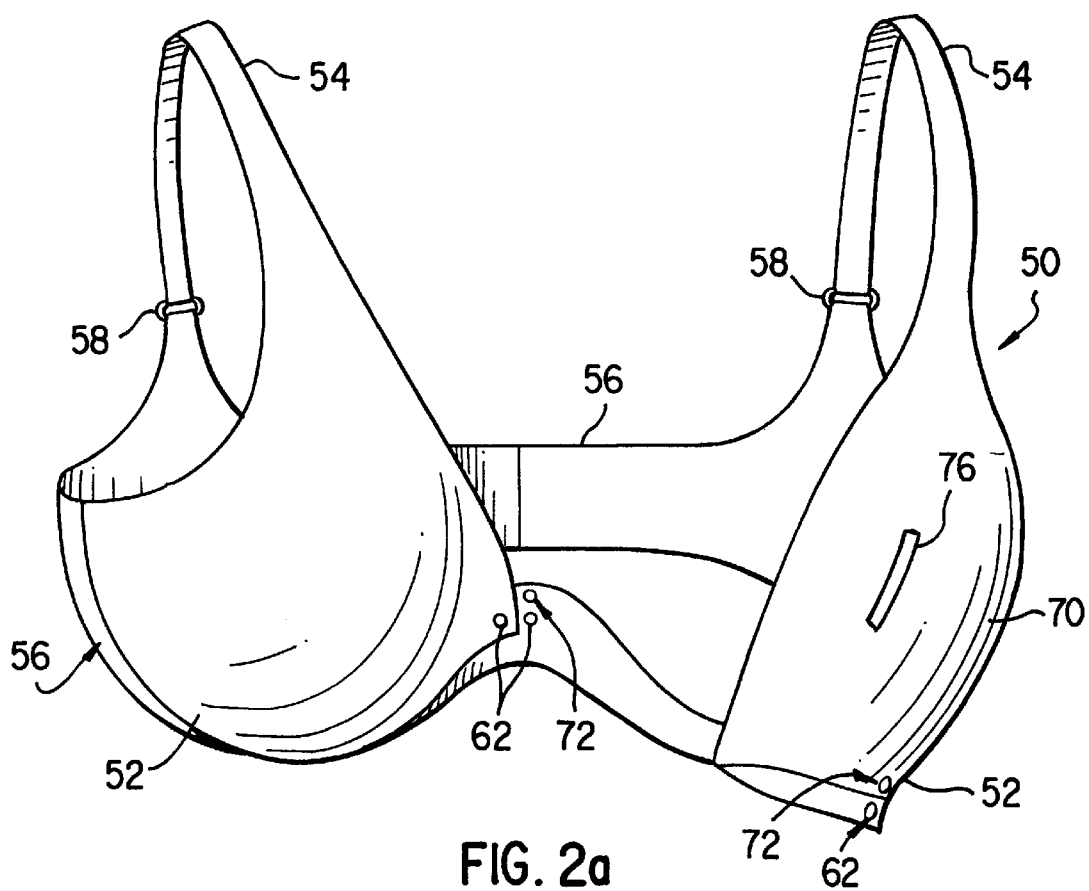
FIGS. 2a and 2b are front perspective views of the hands free pumping and nursing brassiere according to the present invention with the one side open in a nursing configuration.
Figure 2B:
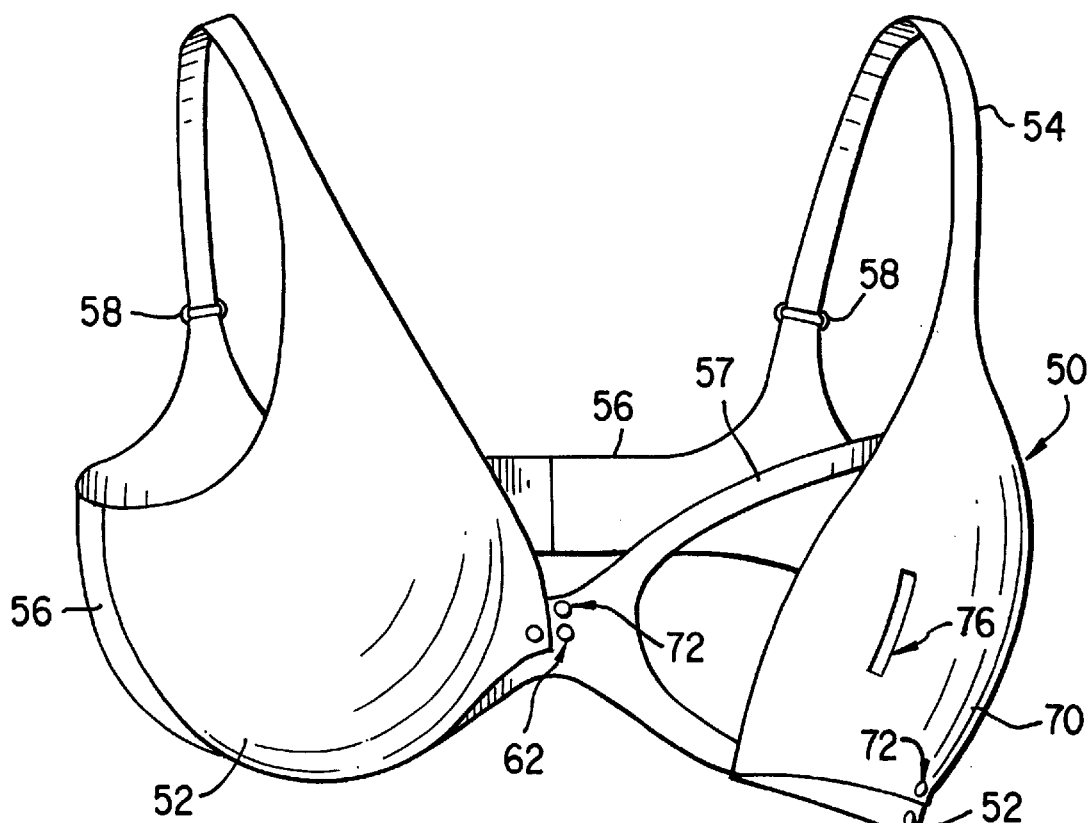
Figure 4:
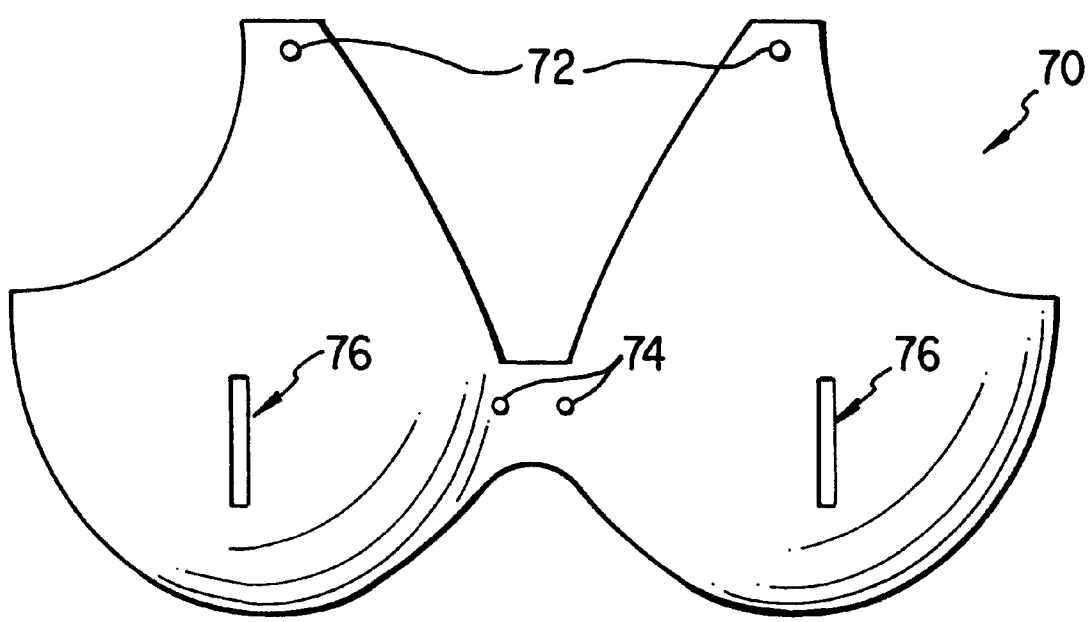
FIG. 4 is a front perspective view of a top opening embodiment of the pumping panel according to the present invention.
Figure 5:
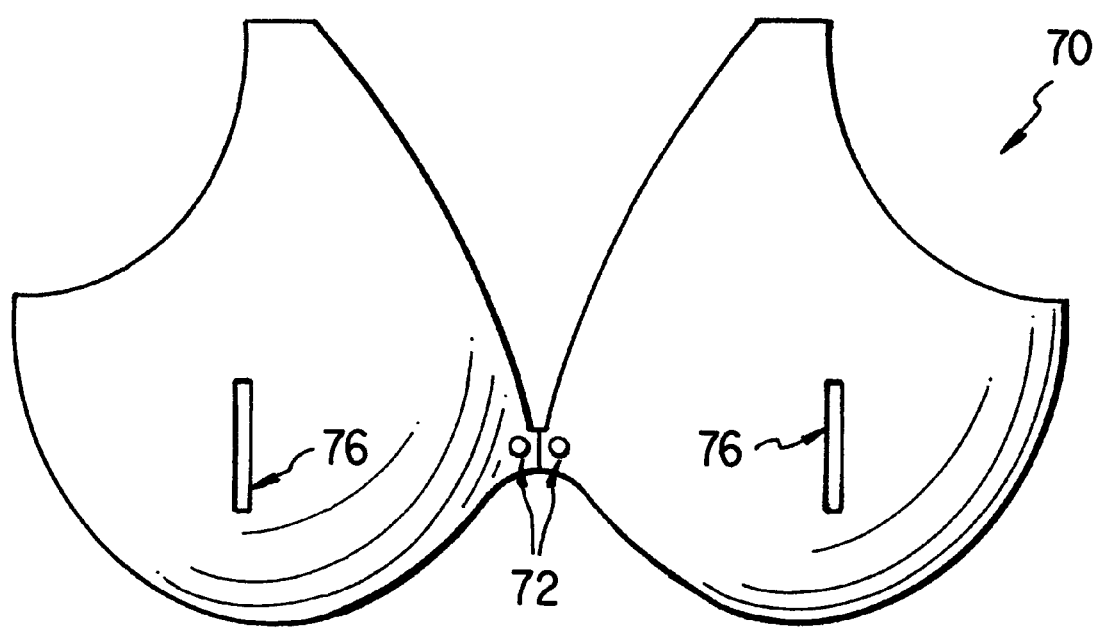
FIG. 5 is a front perspective view of a center opening embodiment of the pumping panel according to the present invention.

The nursing cups 52 may be partially detached from the remainder of the brassiere 50, as shown in FIGS. 2a and 2b, so that a woman may nurse a child. In FIG. 2a, snap or fastener 62 of the left nursing cup 52 is detached so that the left nursing cup 52 may be moved out of the way and the breast exposed sufficiently for a child to nurse. As shown in FIGS. 2a, 2b and 5, a pumping panel 70 is provided behind each nursing cup 52. The pumping panel 70 attaches to the brassiere 50 with its own separate snaps or fasteners 72. Openings 76 may be provided in the pumping panel 70 so that the snaps or fasteners 62 can extend through the pumping panel 70 and hold the nursing cups 52 closed as shown in FIG. 4.

FIG. 2b is similar to FIG. 2a, but shows a brassiere 50 having an additional fabric frame 57 extending from the juncture of the two nursing cups 52 to shoulder strap 54. While only one fabric frame 57 is illustrated, the left and right sides of the brassiere 50 are mirror images of one another, and a second fabric frame 57 would be provided on the left side (not shown). The fabric frame 57 provides additional breast support and support for the pumping panel 70. The brassiere 50 may also have an underwire (not shown) for even more breast support.

FIGS. 2 through 5 further show openings 76 formed in the pumping panel 70. The openings 76 are sized to allow the smaller end of a breast shield to be inserted from the rear, or side of the pumping panel 70 lying adjacent the mother's skin, towards the outside of the brassiere 50. The openings 76, however, are not large enough for the entire pumping shield to pass through. Typically, the pumping shield has a conical shape, and therefore the openings 76 need only be large enough to allow the smallest diameter portion of the pumping shield to protrude. In the illustrated embodiment of FIGS. 2 through 5 the openings 76 are slits, however, the openings 76 may have alternative shapes, such as circles, ovals, triangles, squares, overlapping or combinations thereof, as shown in FIGS. 7a–7e. Here a square slit 76a is shown in FIG. 7a. FIGS. 7b–7e shown circular, oval, triangular and overlapping openings 76b–76e, respectively.

Figure 7E:
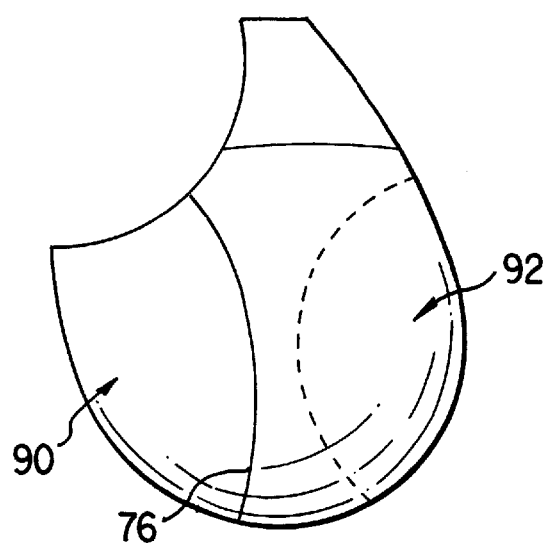
FIGS. 7a–7e are front views of a pumping panel for a right breast according to the present invention showing square, oval, circular and triangular openings, respectively.
Figure 7A:
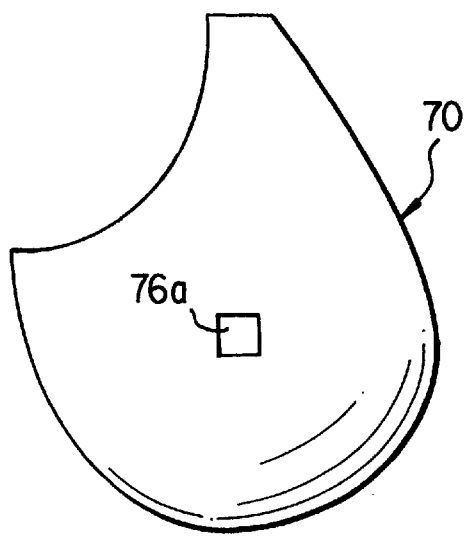
Figure 7B:
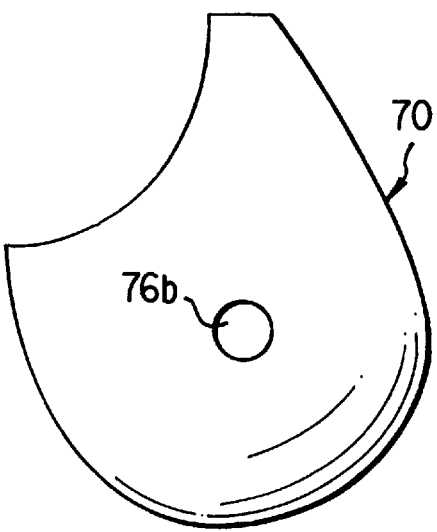
Figure 7C:
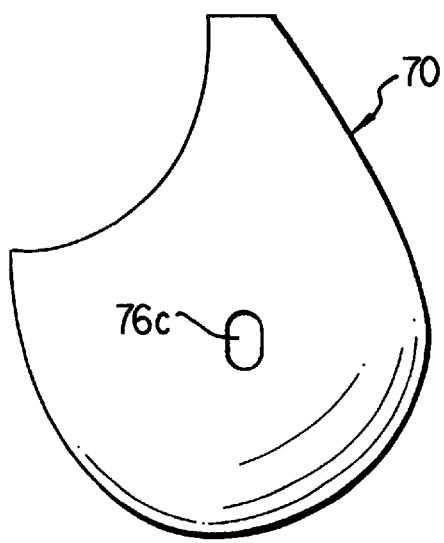
Figure 7D:
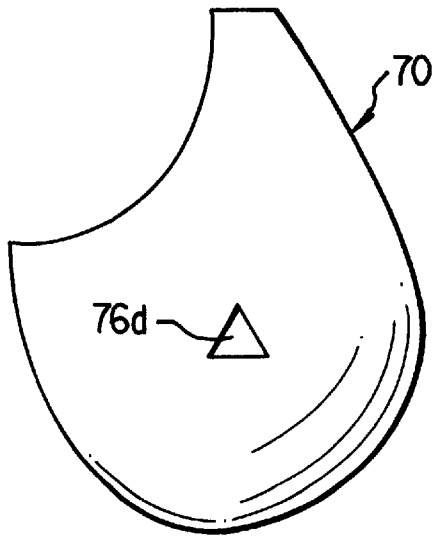

The embodiment shown in FIG. 7e has an opening 76 formed from overlapping pieces of fabric, namely, an underside piece 90 and an outside piece 92. The two fabric pieces 90 and 92 overlap horizontally to form a vertically oriented overlap area 94. The pump shield 80 can be positioned to extend through the opening 76 formed between the two fabric pieces 90 and 92.

Figure 6:
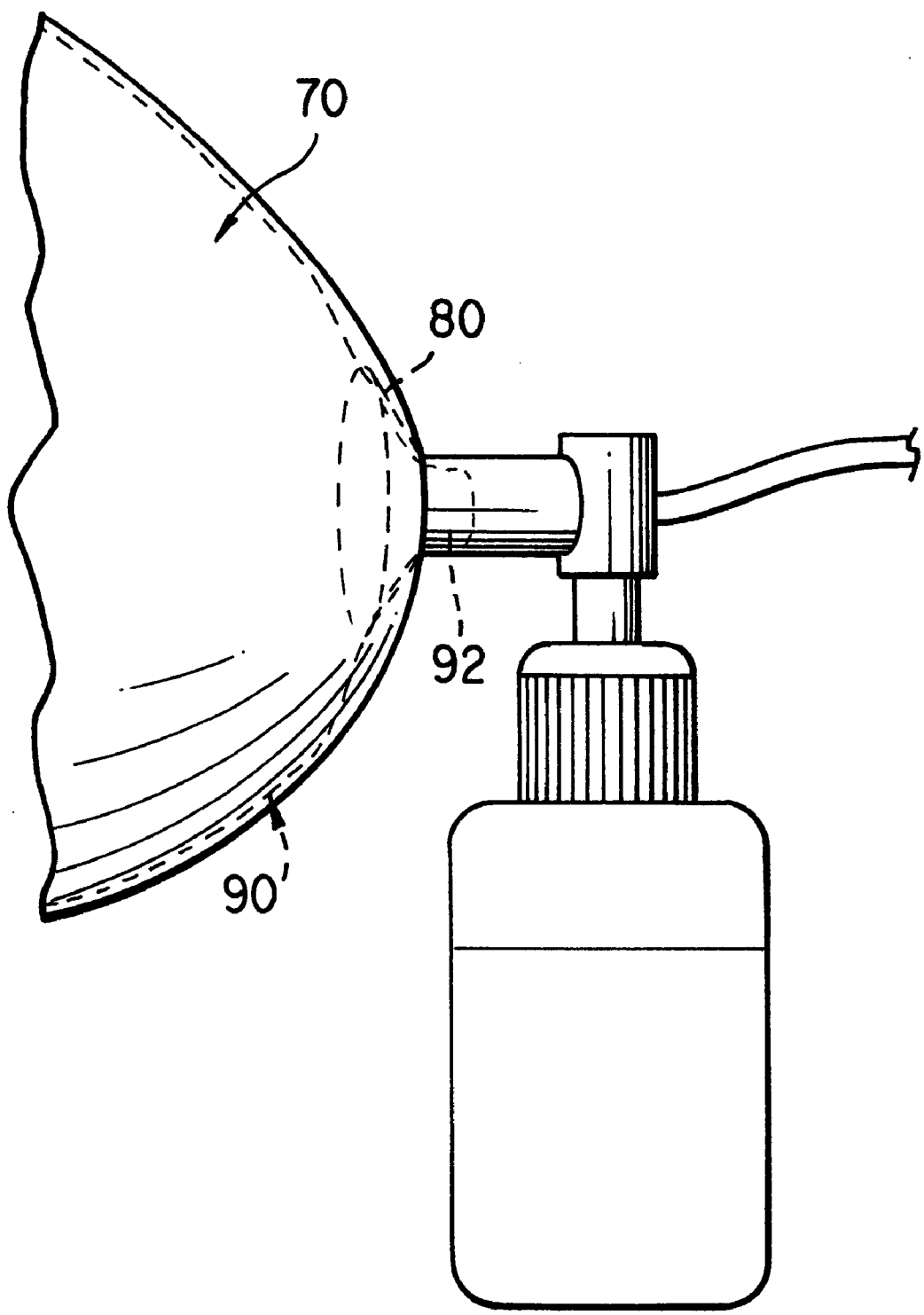
FIG. 6 is a side perspective view of the pumping panel of the present invention positioned over a breast with a breast pump positioned over the nipple.

If a woman wanted to express milk from her left breast using the brassiere 50 of the present invention, she would detach the left nursing cup 52. Then she would detach the left pumping panel 70 and pass the pumping shield 80 through the opening 76 from the inside towards the outside. The left pumping panel 70 would then be refastened to the brassiere 50 so that the pumping panel 70 and the woman's breast 90 hold the pumping shield 80 in place, as shown in FIG. 6. The opening 76 is formed in the pumping panel 70 so that it will lie over the nipple 92 of the breast 90.

Figure 3:
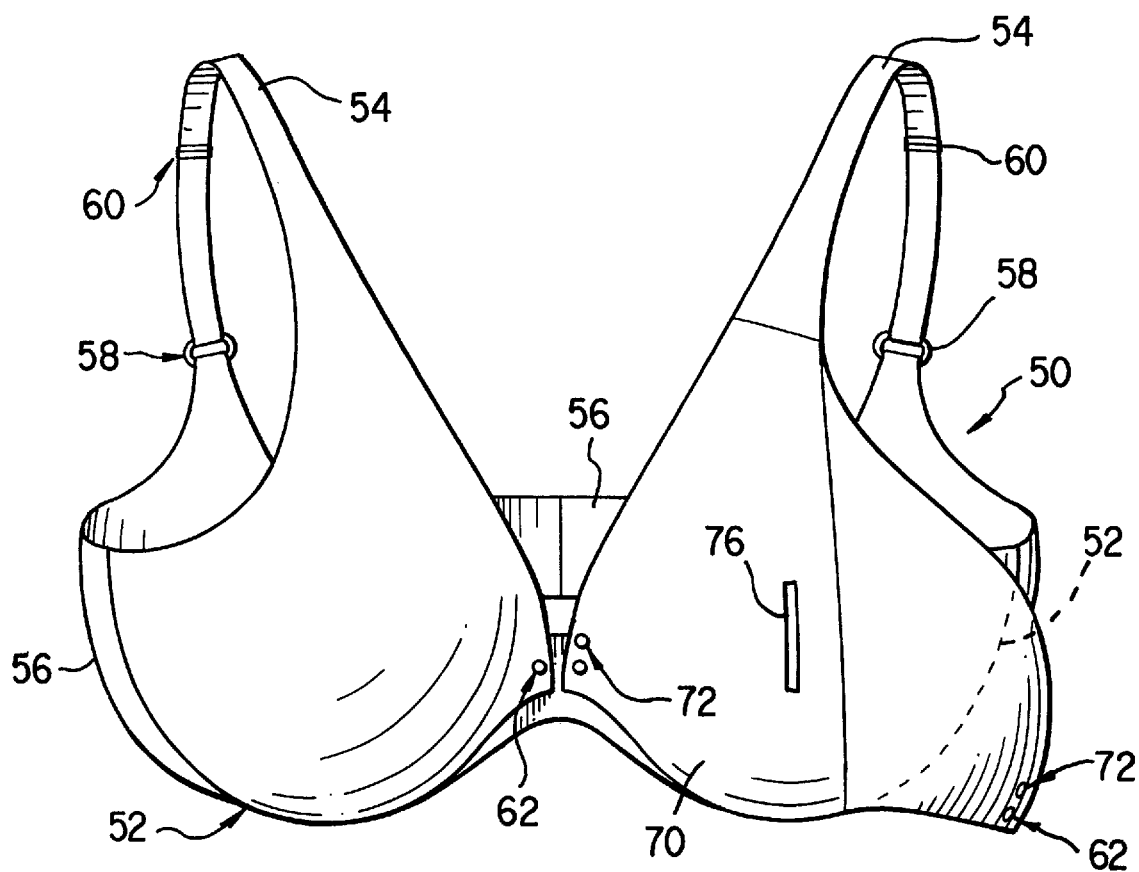
FIG. 3 is a front perspective view of the hands free pumping and nursing brassiere according to the present invention with the one side open in a hands free pumping configuration.

Referring to FIG. 3, the brassiere 50 is shown configured for pumping milk from woman's the left breast. No pump is shown so that the details of the brassiere can be seen. The pumping panel 70 remains attached to fasteners 72, while the fastener 62 for the left nursing cup 52 is detached. As an alternative, a single fastener can be used to connect to nursing cup 52 to the pumping panel 70 and the underlying brassiere base. Such a configuration would consolidate the separate fasteners 62 and 72 into one fastener.

FIG. 4 illustrates a second embodiment of the pumping panel 70 for use in a brassiere 50 that opens from the top, or juncture with the shoulder straps 54. Here the snaps or fasteners 72 are positioned to attach to ends of the shoulder straps 54, and are not placed over the breast bone at the juncture of the left and right nursing cups 52.

While the openings 76 are positioned at the crests of the nursing cups 52 to support the breast shields over the nipples, the pumping panels 70 may provide non-smooth contours under clothes during everyday wearing. To eliminate such unsmooth contours, the pumping panel 70 may be complete detachable from the brassiere 50. For example, each pumping panel 70 may have fasteners 72 located at the juncture of the two nursing cups 52, the juncture with each shoulder strap 54 and the back and side strap 56, as shown in FIG. 5. In this embodiment, the woman would first open one or both nursing cups. Next the pumping panel(s) 70 would be attached using fasteners 72 as the pumping shield is inserted as described previously. Finally the pump would be attached to the pumping shield and milk can be expressed as the pumping panel(s) hold the pump(s) in place.

Having described several embodiments of the hands free pumping and nursing brassiere in accordance with the present invention, it is believed that other modifications, variations and changes will be suggested to those skilled in the art in view of the description set forth above. It is therefor to be understood that all such variations, modifications and changes are believed to fall within the scope of the invention as defined in the appended claims.

What is claimed is:

1. A hands free pumping and nursing brassiere comprising:
   a base support;
   a side and back strap attached to said base support, said base support and said side and back strap fitting around a torso of a woman;
   a pair of nursing cups;
   a pumping panel positioned behind each of said nursing cups;
   first fasteners for detachably securing said nursing cups to said base support; and
   second fasteners for detachably securing said pumping panel to said brassiere;
   each of said pumping panels having a opening at a crest of each of said pumping panels, said opening being sized to permit a narrow end of a tapered pump shield of a breast pump to pass through from an inside of said pumping panel to an outside of said pumping panel when said first fasteners are detached from said base so that said nursing cups are not positioned over said woman's breasts.

2. A hands free pumping and nursing brassiere as recited in claim 1, wherein said first and second fasteners are detachable from said base so that one or both of said pair of nursing cups and said pumping panel do not lie over said woman's breasts to permit direct nursing of a child.

3. A hands free pumping and nursing brassiere as recited in claim 1, wherein said opening is shaped as one of a slit, a circle, a triangle, a square, and a combination of the foregoing shapes.

4. A hands free pumping and nursing brassiere as recited in claim 1, wherein said first fasteners are disposed at a juncture of said nursing cups.

5. A hands free pumping and nursing brassiere as recited in claim 4, wherein said second fasteners are disposed adjacent said first fasteners at said juncture of said nursing cups.

6. A hands free pumping and nursing brassiere as recited in claim 4, wherein said nursing cups are sewn to a portion of said base away from said first fasteners.

7. A hands free pumping and nursing brassiere as recited in claim 1, wherein said second fasteners are disposed so that said pumping panel is completely removable from said brassiere.

8. A hands free pumping and nursing brassiere as recited in claim 1, further comprising shoulder straps attached to said side and back strap, and attached to a top portion of said pair of nursing cups.

9. A hands free pumping and nursing brassiere, as recited in claim 8, wherein said shoulder straps are further attached to a top portion of said pumping panel.

10. A hands free pumping and nursing brassiere comprising:
    a base support;
    a side and back strap attached to said base support, said base support and said side and back strap fitting around a torso of a woman;
    a pair of nursing cups having a first portion permanently attached to one of said brassiere and said nursing cups;
    a pumping panel positioned behind each of said nursing panels;
    first fasteners for detachably securing a second portion of said nursing cups to said brassiere; and
    second fasteners for detachably securing said pumping panel to said brassiere;
    each of said pumping panels having an opening at a crest of each of said pumping panels, said opening being sized to permit a narrow end of a tapered pump shield of a breast pump to pass through from an inside of said pumping panel to an outside of said pumping panel when said first fasteners are detached from said base so that said nursing cups are not positioned over said woman's breasts.

11. A hands free pumping and nursing brassiere as recited in claim 10, wherein said first and second fasteners are detached from said base so that one or both of said pair of nursing cups and said pumping panel are positioned off of said woman's breasts to permit direct nursing of a child.

12. A hands free pumping and nursing brassiere as recited in claim 10, wherein said opening is shaped as one of a slit, a circle, a triangle, a square, and a combination of the foregoing shapes.

13. A hands free pumping and nursing brassiere as recited in claim 10, wherein said first fasteners are disposed at a juncture of said nursing cups.

14. A hands free pumping and nursing brassiere as recited in claim 13, wherein said second fasteners are disposed adjacent said first fasteners at said juncture of said nursing cups.

15. A hands free pumping and nursing brassiere as recited in claim 14, wherein said nursing cups are sewn to a portion of said base away from said first fasteners.

16. A hands free pumping and nursing brassiere as recited in claim 10, wherein said second fasteners are disposed so that said pumping panel is completely removable from said brassiere.

17. A hands free pumping and nursing brassiere as recited in claim 10, further comprising shoulder straps attached to said side and back strap, and attached to a top portion of said pair of nursing cups.

18. A hands free pumping and nursing brassiere, as recited in claim 17, wherein said shoulder straps are further attached to a top portion of said pumping panel.

19. A hands free pumping and nursing brassiere as recited in claim 18, wherein said second fasteners are disposed at tops of said pumping panel adjacent front ends of said shoulder straps.

20. A hands free pumping and nursing brassiere comprising:

a base support;

a side and back strap attached to said base support, said base support and said side and back strap fitting around a torso of a woman;

a pair of nursing cups;

a pumping panel positioned behind each of said nursing panels;

first fasteners for securing said nursing cups to said base support; and second fasteners for securing said pumping panel to said brassiere;

each of said pumping panels having an opening at a crest of each of said pumping panels, said opening being sized to permit a narrow end of a tapered pump shield of a breast pump to pass through from an inside of said pumping panel to an outside of said pumping panel when said first fasteners are detached from said base so that said nursing cups are not positioned over said woman's breasts, wherein said first and second fasteners are detachable from said base so that one or both of said pair of nursing cups and said pumping panel do not lie over said woman's breasts to permit direct nursing of a child, wherein said opening is shaped as one of a slit, a circle, a triangle, a square, and a combination of the foregoing shapes, wherein said first fasteners are disposed at a juncture of said nursing cups, and wherein said nursing cups are sewn to a portion of said base away from said first fasteners.

21. A hands free pumping and nursing brassiere as recited in claim 1, wherein said opening is formed by two overlapping fabric pieces.

22. A hands free pumping and nursing brassiere as recited in claim 10, wherein said opening is formed by two overlapping fabric pieces.

* * * * *